(12) United States Patent
Hitchcock et al.

(10) Patent No.: US 9,795,142 B2
(45) Date of Patent: Oct. 24, 2017

(54) ODOR ELIMINATING SOLUTION

(71) Applicant: Wizard Labs, LLC, Jamestown, NC (US)

(72) Inventors: Wiley William Hitchcock, Greensboro, NC (US); James Michael Puckett, High Point, NC (US)

(73) Assignee: Wizard Labs, LLC, Jamestown, NC (US)

( * ) Notice: Subject to any disclaimer, the term of this patent is extended or adjusted under 35 U.S.C. 154(b) by 0 days.

(21) Appl. No.: 15/195,341

(22) Filed: Jun. 28, 2016

(65) Prior Publication Data

US 2016/0302421 A1    Oct. 20, 2016

Related U.S. Application Data

(62) Division of application No. 13/747,192, filed on Jan. 22, 2013, now Pat. No. 9,392,794.

(60) Provisional application No. 61/588,609, filed on Jan. 19, 2012.

(51) Int. Cl.
| | |
|---|---|
| *A61K 33/38* | (2006.01) |
| *A01N 59/14* | (2006.01) |
| *A01N 59/16* | (2006.01) |
| *A01N 25/04* | (2006.01) |

(52) U.S. Cl.
CPC ............ *A01N 59/16* (2013.01); *A01N 25/04* (2013.01); *A01N 59/14* (2013.01); *A61K 33/38* (2013.01); *A01N 2300/00* (2013.01); *A61K 2300/00* (2013.01)

(58) Field of Classification Search
CPC ......... A61K 33/38; A01N 59/14; A01N 25/04
See application file for complete search history.

*Primary Examiner* — Tracy Liu
(74) *Attorney, Agent, or Firm* — Kilpatrick Townsend & Stockton LLP

(57) ABSTRACT

An odor eliminating solution comprises the active deodorizing and antimicrobial agents of silver nanoparticles dispersed in colloidal suspension in a solution containing excess sodium tetraborate decahydrate, commonly referred to as borax. The silver nanoparticles provide deodorizing and antimicrobial properties through the colloidal dispersion which provides a high surface area to volume ratio for the suspension. The sodium tetraborate decahydrate provides deodorizing and antimicrobial properties through its co-complexing ability with various substances. The combination of both provides the present invention with long term stability and deodorizing and antimicrobial activity. Furthermore, the present invention includes the method for formulating the odor eliminating solution through the combination of a silver nanoparticle source solution and an aqueous sodium tetraborate solution which results in a chemical reaction that synthesizes the silver nanoparticles from the silver cations. The resulting odor eliminating solution can be utilized independently or combined with existing odor management products.

3 Claims, 7 Drawing Sheets

| Active Agents | Optimized Concentration Ranges (mM) | Weight by Volume |
|---|---|---|
| $Ag_n$ | 0.125mM to 0.250mM | 13.48 mg/L to 26.96 mg/L |
| $Na_2[B_4O_5(OH)_4] \cdot 8H_2O$ | 35.0mM to 50.0mM | 26.96 g/L to 38.137 g/L |

FIG. 1B

Sodium Tetraborate Decahydrate

| | |
|---:|:---|
| CAS number: | 1303-96-4 |
| Formula: | $Na_2[B_4O_5(OH)_4] \cdot 8H_2O$ |
| Formula Weight: | 381.37 g/mol |
| Density: | 1.73 g/cm$^3$ |
| Melting Point: | 1016.15 K |
| Boiling Point: | 1575.15 K |

FIG. 2B

Silver Nitrate

| | |
|---:|:---|
| CAS number: | 7761-88-8 |
| Formula: | $AgNO_3$ |
| Formula Weight: | 169.87 g/mol |
| Density: | 4.35 g/cm$^3$ |
| Melting Point: | 485.15 K |
| Boiling Point: | 717.15 K |

FIG. 3B

ODOR ELIMINATING SOLUTION

This application is a divisional of U.S. application Ser. No. 13/747,192, filed Jan. 22, 2013, which claims the benefit of and priority under 35 U.S.C. §119(e) to U.S. Provisional Patent Application Ser. No. 61/588,609 filed on Jan. 19, 2012, the disclosures of which are herein incorporated in their entirety.

FIELD OF THE INVENTION

The present invention generally relates to an odor management composition, more specifically to a deodorizing solution that reduces and eliminates odors as well as the microorganisms responsible for creating said odors through the use of a formulated colloidal silver tetraborate solution.

BACKGROUND OF THE INVENTION

It is well known that various odor management compositions exist. These odor management compositions can be divided into three categories that are based on their functionality. These categories of odor management compositions are defined as odor masking compositions, which masks odors through the use of fragrances or perfumes, deodorizing/sanitizing compositions, which bind to odors or eliminate the microorganism that are responsible for the production of said odors, and combination odor masking and deodorizing/sanitizing compositions, which bind to odors and eliminate the microorganisms responsible for the production of said odors, as well as introducing a perfume or fragrance. Odor masking compositions primarily function by providing a large quantity of a perfume or fragrance that overwhelms the senses, masking odors without removing or modifying the source of said odor. Deodorizing/sanitizing compositions function by containing active agents that function in a deodorizing and antimicrobial capacity. The deodorizing agents chemically bind to existing odors deactivating them, while the antimicrobial agents are responsible for eliminating the microorganisms responsible for the production of said odors. Combination odor masking and deodorizing/sanitizing compositions are provided with both a deodorizing/sanitizing agent and an odor masking composition that eliminates the source of a particular odor while providing an additional fragrance or perfume to the area of application. Of these odor management compositions, deodorizing/sanitizing compositions are of particular interest due to their various applications and incorporation into new and existing odor management systems.

Current deodorizing/sanitizing compositions can be formulated using a plurality of active deodorizing/sanitizing agents. One of these active sanitizing agents includes sodium tetraborate decahydrate, commonly known as "borax." Borax is a boron salt that has the chemical formula $Na2[B_4O_5(OH)_4]\cdot 8H_2O$ in solution. Borax is able to function as a deodorizing/sanitizing agent as a result of its co-complexing ability that enables it to stably bind with various substances forming complex ions. The ability to form complex ions enables borax to function as a deodorizing agent but additionally grants it antimicrobial properties. These antimicrobial properties are a result of the borax formed complex ions inhibiting key metabolic pathways of several microorganisms.

Another active deodorizing/sanitizing agent is colloidal silver. Colloidal silver is metallic silver nanoparticles formed after ionization of silver or as a result of a chemical reaction which synthesize zero valent silver from mono valent silver cations. The zero valent silver cations that are formed, disperse in a colloidal suspension, wherein the colloidal suspension provides the silver nanoparticles separated between 10 nanometers (nm) to 100 nanometers (nm) apart from another silver nanoparticle. Through this unique arrangement, silver nanoparticles have unique optical, electrical and thermal properties, in part due to significant surface area to volume ratio. The colloidal dispersal of the silver nanoparticles grants a solution with silver nanoparticles with deodorizing and antimicrobial properties. The deodorizing properties are provided by the ability of the silver nanoparticles to react with substances more frequently due to the surface area to volume ratio. The antimicrobial properties are provided by the ability of the silver nanoparticles inhibiting oxygen metabolism in various microorganisms.

While odor management compositions containing colloidal silver or borax are well known, an odor management composition containing a combination of these two agents is not currently available. A possible explanation for the lack of a combined colloidal silver borax solution could be attributed to the long term stability of the combined solution, wherein the long term stability may refer to the inactivity of the deodorizing/sanitizing agents or to the formation of a precipitate over time. Another potential explanation could be due to the formulation of the combined colloidal silver borax solution and potential difficulties in creating said combined colloidal silver borax solution.

It is therefore the object of the present invention to provide an odor management compositions and the method for creating said odor management composition containing the active deodorizing and antimicrobial agents of silver nanoparticles in a colloidal suspension, commonly known as colloidal silver, and sodium tetraborate decahydrate, commonly known as borax. The present invention provides a method for creating the combination colloidal silver borax solution through an in situ reaction that occurs at standard temperature and pressure values, between a formulated borax solution and a formulated silver nanoparticle source solution. The resulting colloidal silver borax solution results in a deodorizing and antimicrobial solution that eliminates various odors and reduces microbial presence responsible for the production of said odors. Additionally, the colloidal silver borax solution has long term shelf stability.

BRIEF DESCRIPTIONS OF THE DRAWINGS

FIG. 1B is a reference table displaying the optimal concentration ranges and weight by volume of the active agents as per the current embodiment of the present invention.

FIG. 2B is a reference table displaying the properties of sodium tetraborate decahydrate.

FIG. 3B is a reference table displaying the properties of silver nitrate.

DETAIL DESCRIPTIONS OF THE INVENTION

All illustrations of the drawings are for the purpose of describing selected versions of the present invention and are not intended to limit the scope of the present invention.

Figure 1A:
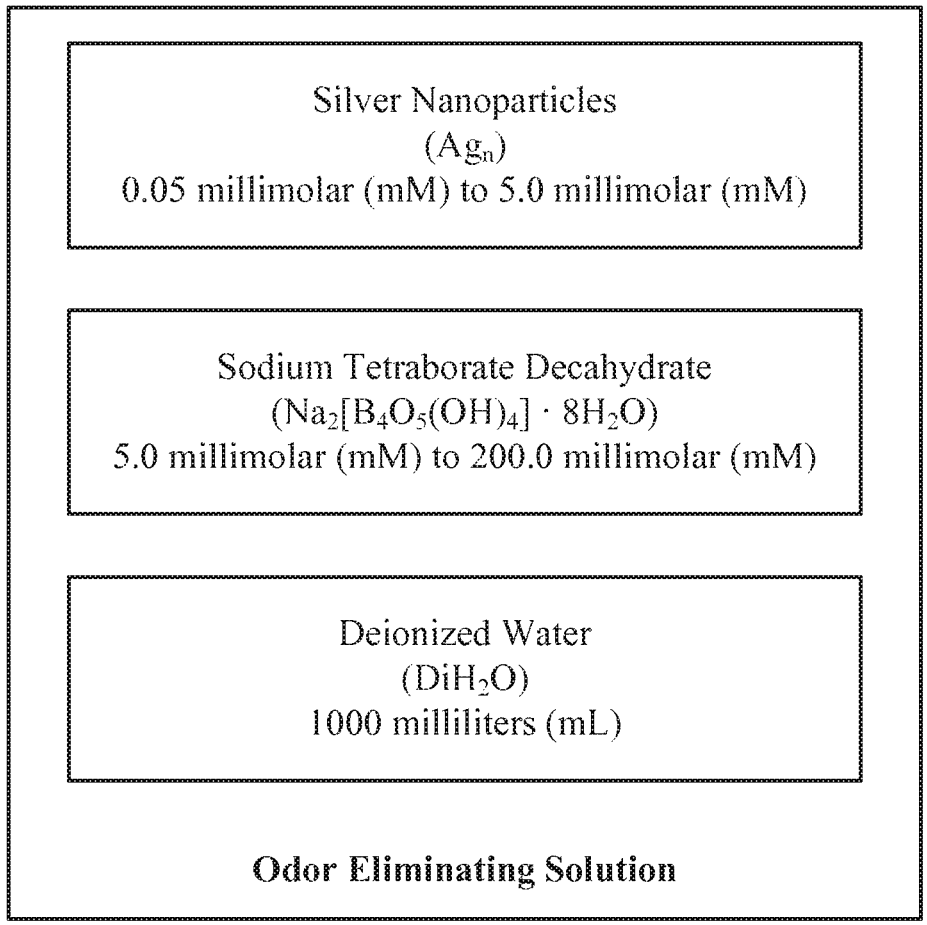
FIG. 1A is a block diagram displaying the active agents of the odor eliminating solution as per the current embodiment of the present invention.

Referencing FIG. 1A, the present invention is an odor eliminating solution and the method to create said odor eliminating solution for the purposes of reducing and/or eliminating unwanted odors. The odor eliminating solution in its current embodiment comprises silver nanoparticles ($Ag_n$), sodium tetraborate decahydrate ($Na_2[B_4O_5(OH)_4] \cdot 8H_2O$), and deionized water. The silver nanoparticles function as one of the deodorizing agents in the odor eliminating solution. The sodium tetraborate decahydrate is provided in excess and functions as another deodorizing agent in the odor eliminating solution. The deionized water is the purified aqueous medium that has had mineral impurities chemically removed in order to reduce chemical interference with the silver nanoparticles and the sodium tetraborate decahydrate.

Figure 3A:
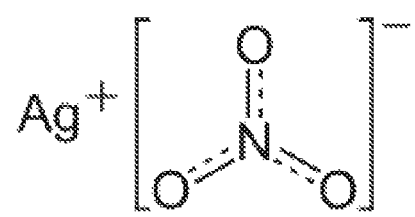
FIG. 3A is an image displaying a line drawing representation of silver nitrate.

Referencing FIGS. 3A and 3B, in the present invention the silver nanoparticles are synthesized from a silver nanoparticles source. The silver nanoparticle source is a silver salt that provides mono valent silver cations ($Ag^+$) utilized in a reduction oxidization (redox) reaction for the purposes of creating zero valent silver nanoparticles ($Ag_n$). In the present invention the silver nanoparticle ($Ag_n$) source is provided by Silver Nitrate ($AgNO_3$). Silver Nitrate, CAS No. 7761-88-8, is a silver salt that dissolves in solution forming mono valent silver cations ($Ag^+$) and nitrate anions ($NO_3^-$). The silver nanoparticles synthesized from silver nitrate function as a deodorizing and antimicrobial agent that inhibit microbial growth and binds to odors.

Referencing FIGS. 1A and 1B, in the present invention the silver nanoparticles are provided in the odor eliminating solution at a concentration ranging between 0.05 millimolar (mM) to 5.0 millimolar (mM). The concentration range provided for the silver nanoparticles in solution was determined as optimal when dissolved in the sodium tetraborate decahydrate solution. While the concentration of the silver nanoparticles can be found within the range of 0.05 mM to 5.0 mM, the preferred embodiment of the present invention provides the silver nanoparticles with a concentration ranging between 0.125 mM to 0.250 mM. It should be noted that the values calculated for the concentration of silver nanoparticles in solution were derived from the expected yield of the silver nanoparticles from the redox reaction between sodium tetraborate decahydrate and silver nitrate. The balanced chemical equation for the reaction between sodium tetraborate decahydrate and silver nitrate is provided below:

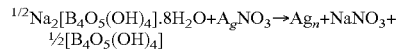

$$^{1/2}Na_2[B_4O_5(OH)_4] \cdot 8H_2O + A_gNO_3 \rightarrow Ag_n + NaNO_3 + \tfrac{1}{2}[B_4O_5(OH)_4]$$

In the present invention, the silver nanoparticles are dispersed in colloidal suspension. The colloidal suspension provides the silver nanoparticles with a separation distance of 10 nanometers (nm) to 100 nanometers (nm) from another neighboring silver nanoparticle. The dispersion of the silver nanoparticles provides increased chemical activity to the silver nanoparticles by increasing the surface area to volume ratio. The increased surface area to volume ration for the silver nanoparticles further provides increased antimicrobial and bactericidal properties. The antimicrobial and bactericidal properties are due to increased penetration through bacterial membranes, which enables silver nanoparticles to function as a catalyst, which disables the enzymes that bacteria need for their oxygen metabolism. This reduction in microbial growth directly contributes to a reduction of unwanted odors.

Figure 2A:
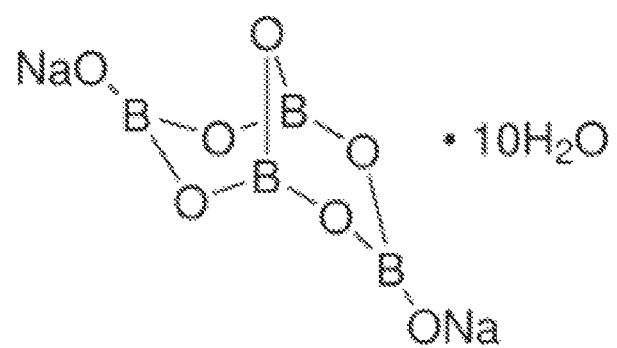
FIG. 2A is an image displaying a line drawing representation of sodium tetraborate decahydrate.

Referencing FIGS. 2A and 2B, in the present invention the Sodium Tetraborate Decahydrate $Na_2[B_4O_5(OH)_4] \cdot 8H_2O$), commonly known as "borax", functions as deodorizing agent as well as a reagent used to synthesize silver nanoparticles. Sodium tetraborate decahydrate is the reducing agent that donates electrons ($e^-$) to the mono valent silver cations ($Ag^+$) during the redox reaction that forms the silver nanoparticles ($Ag_n$). The excess sodium tetraborate decahydrate found in solution after the redox reaction serves as the weak buffer that stabilizes the silver nanoparticles in suspension but additionally function as a deodorizing agent that binds and absorbs odors. The sodium tetraborate decahydrate, CAS No. 1303-96-4, is a boron salt that dissolves in solution forming sodium cations ($Na^+$) and tetraborate anions ($[B_4O_5(OH)_4]^{2-}$).

Referencing FIGS. 1A and 1B, in the present invention the sodium tetraborate decahydrate is provided in the odor eliminating solution at a concentration ranging between 5.0 millimolar (mM) to 200.0 millimolar (mM). The concentration range provided for the sodium tetraborate decahydrate was determined to be the optimal range for dissolving and reacting with the aqueous solution of silver nitrate. The concentration range for the sodium tetraborate decahydrate provides the reactant in excess allowing the un-reacted excess to function as a buffering agent as well as a deodorizing agent. The buffering ability provided by the concentration range of the sodium tetraborate decahydrate provides the odor eliminating solution with a pH above 8. This pH range provides a stabilizing effect for the colloidal suspension of silver nanoparticles. The deodorizing effects of the excess sodium tetraborate decahydrate are provided by the sodium tetraborate decahydrate co-complexing ability which permits it to bind to various substances including those responsible for causing odors. While the concentration of sodium tetraborate decahydrate is found within the range of 5.0 mM to 200 mM, the preferred embodiment of the present invention provides the sodium tetraborate decahydrate at a concentration ranging between 35.0 mM to 50.0 mM. With the concentration range of the sodium tetraborate decahydrate being between 35.0 mM to 50.0 mM the pH of the solution is found ranging between 9 to 10. It should be noted that the values calculated for the concentrations of sodium tetraborate decahydrate were derived from initial quantities of sodium tetraborate decahydrate dissolved in deionized water.

In the present invention the formulation of the odor eliminating solution provides a molar ratio between the sodium tetraborate decahydrate and the silver nanoparticle source ranging between 200:1(35.0 mM sodium tetraborate decahydrate: 0.125 mM silver nitrate) to 280:1(50.0 mM sodium tetraborate decahydrate: 250 mM silver nitrate). The molar ratios provide the optimal range for the reagents that would result in the best odor elimination, formulation stability, silver nanoparticle size, and length of the reaction. It should be noted that the range of molar ratios was determined using the initial quantities of silver nitrate and sodium tetraborate decahydrate and that the optimal range that provides the best odor elimination solution, the best formulation stability, the best silver nanoparticle size, and the preferred length of the reaction was found through experimentation.

Figure 4:
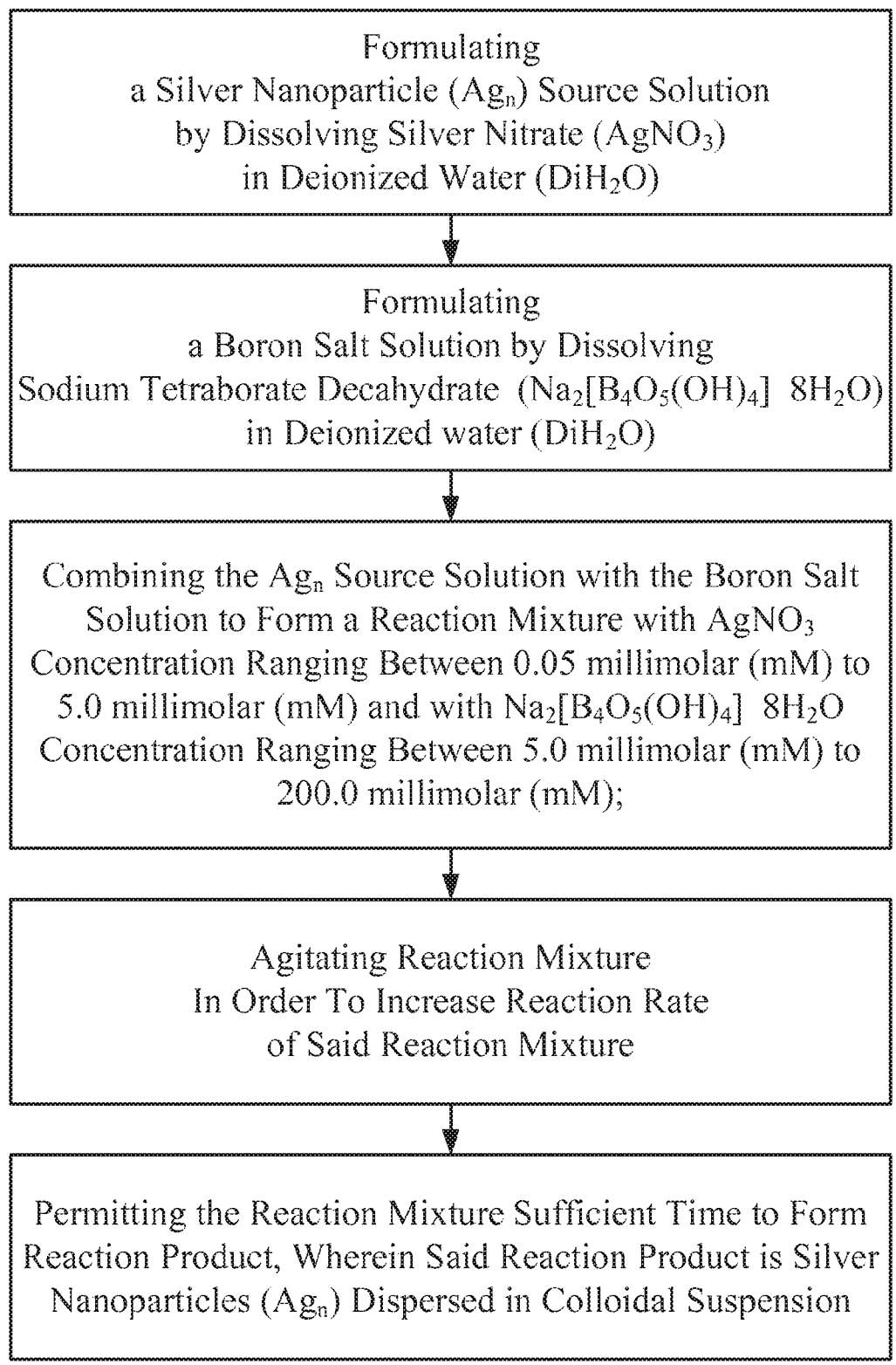
FIG. 4 is a flow chart diagram displaying the method steps involved in formulating the present invention.

Referencing FIG. 4, in the present invention the odor eliminating solution functions by utilizing the chemical properties of the silver nanoparticles and the sodium tetraborate decahydrate ("borax") in said solution to reduce and/or eliminate odors by binding to or absorbing said odors as well as reducing or eliminating microorganisms responsible for the formation of unwanted odors. The odor eliminating solution is created through a redox reaction that utilizes sodium tetraborate decahydrate, in excess, as the reducing agent and aqueous silver nitrate solution as the silver nanoparticle ($Ag_n$) source. The method for creating the odor eliminating solution comprises the steps of formulating a silver nanoparticle ($Ag_n$) solution through the dissolution of silver nitrate in deionized water; formulating a boron salt solution by dissolving sodium tetraborate decahydrate $Na_2[B_4O_5(OH)_4].8H_2O)$ in deionized water; combining the $Ag_n$ source solution with the alkali salt solution to form a reaction mixture with AgNO3 concentration ranging between 0.05 millimolar (mM) to 5.0 millimolar (mM) and with $Na_2[B_4O_5(OH)_4].8H_2O$ concentration ranging between 5.0 millimolar (mM) to 200.0 millimolar (mM); agitating reaction mixture in a capped vessel in order to increase reaction rate of said reaction mixture; permitting the reaction mixture sufficient time to form reaction product, wherein said reaction product is silver nanoparticles ($Ag_n$) dispersed in colloidal suspension in a solution containing excess sodium tetraborate decahydrate.

In the present invention the formulation of the silver nanoparticle source solution comprises the steps of dissolving a quantity of silver nitrate in deionized water. The quantity of silver nitrate that is required to formulate the silver nanoparticle source solution is dependent on the desired concentration of silver nanoparticles in the finalized solution. The relation between the silver nitrate and the silver nanoparticles is provided as a 1:1 ratio, wherein 1.0 mole of silver nitrate should yield 1.0 mole of silver nanoparticles. In this capacity silver nitrate functions as the limiting reagent. In the current embodiment of the present invention a silver particle source solution of aqueous silver nitrate is created by dissolving a quantity of silver nitrate, CAS No. 7761-88-8, ranging between 21.2 milligrams (mg) to 42.4 milligrams (mg) in a 500 milliliter (mL) solution of deionized water. The resulting dissolutions of silver nitrate results in a silver cation ($Ag^+$) concentration ranging between 0.250 mM to 0.500 mM in the silver nanoparticle source solution. It should be noted that the formulation of the silver nanoparticle source solution occurs at standard conditions for temperature and pressure (STP) unless otherwise noted.

In the present invention the formulation of the boron salt solution comprises the steps of dissolving a quantity of the sodium tetraborate decahydrate in deionized water. The quantity of sodium tetraborate decahydrate utilized to formulate the boron salt solution is dependent on the solubility and the reaction kinetics regarding the formation of the silver nanoparticles. The solubility of sodium tetraborate decahydrate has a proportional relation with temperature, wherein temperature increases are proportional to increased solubility of sodium tetraborate decahydrate. The reaction rate for the formation of the silver nanoparticles is dependent on the molar ratio between the silver nitrate and the sodium tetraborate decahydrate favoring excess sodium tetraborate decahydrate. In the current embodiment of the present invention a boron salt solution of aqueous sodium tetraborate decahydrate is created by dissolving a quantity of sodium tetraborate decahydrate ranging between 13.35 grams to 19.07 grams in a 500 mL solution of deionized water at standard condition for temperature and pressure (STP). The resulting dissolution of sodium tetraborate decahydrate results in a concentration ranging between 70 mM to 100 mM in the boron salt solution.

In the present invention the silver nanoparticle source solution is combined with the boron salt solution to form a reaction mixture that contains a silver nitrate concentration ranging between 0.05 millimolar (mM) to 5.0 millimolar (mM) and with the sodium tetraborate decahydrate concentration ranging between 5.0 millimolar (mM) to 200.0 millimolar (mM). Due to the reactivity of the reaction mixture, the silver nanoparticle source solution should be added to the boron salt solution. In the current embodiment of the present invention equal volumes of the silver nanoparticle solution and the boron salt solution are provided resulting in a molar concentration range of the silver cation ($Ag^+$) concentration ranging between 0.125 mM to 0.250 mM with the sodium tetraborate decahydrate concentration ranging between 35.0 mM to 50.0 mM. It should be noted that the combination of the silver nanoparticle source solution and the boron salt solution occur at standard conditions for temperature and pressure (STP) unless otherwise noted.

In the present invention the reaction mixture comprising the silver nanoparticle source solution and the boron salt solution is agitated in order to increase the rate at which the reaction progresses. Agitation of the reaction mixture is provided in order to increase the collision frequency between the silver cations ($Ag^+$) and the tetraborate anions ($[B_4O_5(OH)_4]^{2-}$) resulting in the reduction of the mono valent silver cation ($Ag^+$) into the zero valent silver nanoparticle ($Ag_n$). Agitation of the reaction mixture can be accomplished through several means but the means of agitation are dependent on the container in which the silver nanoparticle source solution and the boron salt solution are combined in. These agitation means can include but are not limited to vortexing the reaction mixture in capped glassware, as well as stirring the reaction mixture on a stir plate with a magnetic stir bar. In the preferred embodiment of the present invention the reaction mixture is agitated by sealing the reaction mixture within a container and shaking the container for a few seconds. It should be noted that while agitation of the reaction mixture is provided as a mechanical means of increase the reaction rate of the reaction mixture, alternative non mechanical means could be used to accomplish the same increase in reaction rate. An alternative means of increasing the reaction rate can be accomplished by adding heat to the reaction mixture. Heat applied to the reaction mixture would increase collisions resulting in increased reaction kinetics. Still another means to increase the reaction rate for the reaction mixture is to combine the silver nanoparticle source solution with a heated boron salt solution on a stir plate. The combination of the silver nanoparticle source solution with the heated boron salt solution on a stir plate would result in a high collision frequency and would subsequently result in an increased reaction rate. Furthermore, it should be noted that the agitation of the reaction mixture occurs at standard conditions for temperature and pressure (STP) unless otherwise noted.

In the present invention the reaction mixture is permitted sufficient time in order for the reaction to complete forming the reaction products. The reaction products that are formed during this step are the silver nanoparticles. The silver nanoparticles are found dispersed in a colloidal suspension in a solution that consists of excess aqueous sodium tetraborate decahydrate. This step is provided to ensure that the reaction completes synthesizing the silver nanoparticles from the silver nitrate solution but additionally permits the dispersion of the silver nanoparticles in a colloidal suspension. This step additionally prevents un-reacted silver nitrate from being dispersed with the odor eliminating solution. It should be noted that the aforementioned step of permitting sufficient time for the reaction to complete can occur simultaneously as well as in tandem to the agitation of the reaction mixture.

In the present invention the completed reaction mixture containing the silver nanoparticles in colloidal suspension and the excess aqueous sodium tetraborate decahydrate can be utilized independently or incorporated into various existing applications depending on the formulation of the reaction mixture. For independent utilization of the odor eliminating solution, a desired area is selected and the odor eliminating solution is evenly dispersed within said area to reduce or eliminate a particular odor. The dispersal of the odor eliminating solution can be accomplished through several means which include but are not limited to misting a desired area, swabbing a desired area, soaking a material with the odor eliminating solution, as well as any combination thereof. The odor eliminating solution may be utilized as a means to reduce or eliminate odors in areas that include but are not limited to furniture, carpets, animal beds, vehicle upholstery, as well as various textiles. Due to the stability and the chemical properties of the formulation, the odor eliminating solution will have a prolonged effective period. The prolonged effectiveness occurs as a result of the antimicrobial and bactericidal properties of the colloidal suspension of silver nanoparticles and the sodium tetraborate decahydrate. The solution is able to eliminate odors present at administration and is further able to limit to formation of new odors through the antimicrobial properties.

In the present invention, the odor eliminating solution may be formulated for incorporation into existing applications and as an active deodorizing and antimicrobial agent. The formulation of the present invention would provide the silver nanoparticles and the sodium tetraborate decahydrate at such concentrations optimally suited for incorporation into existing products that include but are not limited to liquid soaps, deodorant stick, shampoos, and any other existing product that would greatly benefit from the deodorizing and antimicrobial properties of the present invention. It should be noted that the present invention may additionally be formulated as a direct replacement for the aqueous portions of products that include but are not limited to deodorant stick formulations, liquid hand soaps, and existing deodorizing sprays.

In the current embodiment of the present invention the formulation of the silver nanoparticle source solution, the boron salt solution, and the combination thereof, occurs in a container that has a low reactivity with the aforementioned solutions. The low reactivity provided by the container is due to the material construction which provides long term stability and a negligible amount of reactivity with solutions. It should be noted that while no specific materials are described, the intended function can be accomplished by a plurality of materials that include but are not limited to glassware, Polyethylene terephthalate (PETE), low density polyethylene (LDPE) as well as any combination thereof.

Although the invention has been explained in relation to its preferred embodiment, it is to be understood that many other possible modifications and variations can be made without departing from the spirit and scope of the invention as hereinafter claimed.

What is claimed is:

1. A method of creating and utilizing an odor eliminating solution comprises the steps of:
    (1) formulating a silver nanoparticle ($Ag_n$) source solution by dissolving Silver Nitrate ($AgNO_3$) in deionized water ($DiH_2O$);
    (2) formulating a boron salt solution by dissolving sodium tetraborate decahydrate ($Na_2[B_4O_5(OH)_4]\cdot 8H_2O$) in deionized water ($DiH_2O$);
    (3) combining the $Ag_n$ source solution with the boron salt solution to form a reaction mixture with $AgNO_3$ concentration ranging between 0.05 millimolar (mM) to 5.0 millimolar (mM) and with $Na_2[B_4O_5(OH)_4]\cdot 8H_2O$ concentration ranging between 5.0 millomolar (mM) to 200.0 millimolar (mM);
    (4) agitating reaction mixture of step (3) in order to increase reaction rate of said reaction mixture; and
    (5) permitting the reaction mixture sufficient time to form reaction product, wherein said reaction product is silver nanoparticles ($Ag_n$) dispersed in colloidal suspension.

2. The method of creating and utilizing an odor eliminating solution of claim 1, wherein $AgNO_3$ is present at a concentration ranging between 0.125 mM to 0.250 mM.

3. The method of creating and utilizing an odor eliminating solution of claim 1, wherein $Na_2[B_4O_5(OH)_4]\cdot 8H_2O$ is present at a concentration ranging between 35.0 mM to 50 mM.

* * * * *